US012594291B2

(12) United States Patent
Domankevich et al.

(10) Patent No.: US 12,594,291 B2
(45) Date of Patent: Apr. 7, 2026

(54) INTRATUMORAL ALPHA-EMITTER RADIATION AND ACTIVATION OF CYTOPLASMATIC SENSORS FOR INTRACELLULAR PATHOGEN

(71) Applicant: ALPHA TAU MEDICAL LTD., Tel Aviv (IL)

(72) Inventors: Vered Domankevich, Hod Hasharon (IL); Yona Keisari, Ramat Gan (IL); Itzhak Kelson, Tel Aviv (IL)

(73) Assignee: Alpha Tau Medical Ltd, Jerusalem (IL)

( * ) Notice: Subject to any disclaimer, the term of this patent is extended or adjusted under 35 U.S.C. 154(b) by 982 days.

(21) Appl. No.: 17/288,926

(22) PCT Filed: Oct. 31, 2019

(86) PCT No.: PCT/IB2019/059331
§ 371 (c)(1),
(2) Date: Apr. 27, 2021

(87) PCT Pub. No.: WO2020/089819
PCT Pub. Date: May 7, 2020

(65) Prior Publication Data
US 2021/0379096 A1     Dec. 9, 2021

Related U.S. Application Data

(60) Provisional application No. 62/753,930, filed on Nov. 1, 2018.

(51) Int. Cl.
*A61N 5/10*          (2006.01)
*A61K 31/167*       (2006.01)
(Continued)

(52) U.S. Cl.
CPC ........ *A61K 31/7068* (2013.01); *A61K 31/167* (2013.01); *A61K 31/4406* (2013.01);
(Continued)

(58) Field of Classification Search
None
See application file for complete search history.

(56) References Cited

U.S. PATENT DOCUMENTS 8,372,818 B2    2/2013  Shir et al.
8,821,364 B2    9/2014  Fisher et al.
(Continued)

FOREIGN PATENT DOCUMENTS

CN          105031648 A     11/2015
EP            1252306 B1      7/2009
(Continued)

OTHER PUBLICATIONS

CN Application # 2019800709663 Office Action dated Nov. 4, 2022.
(Continued)

*Primary Examiner* — Thaddeus B Cox
(74) *Attorney, Agent, or Firm* — Meitar Patents Ltd.; Daniel Kligler

(57)          ABSTRACT
A method of treating a patient with a tumor, and kits (200) for such treatment. The method includes administering, to the patient, a substance (204) which activates cytoplasmatic sensors for intracellular pathogen in the tumor and treating the tumor with intra-tumoral alpha-emitter radiotherapy within two weeks of administering the substance which activates cytoplasmatic sensors for intracellular pathogen in the tumor.

63 Claims, 2 Drawing Sheets

(51) Int. Cl.

| | |
|---|---|
| A61K 31/4406 | (2006.01) |
| A61K 31/454 | (2006.01) |
| A61K 31/497 | (2006.01) |
| A61K 31/675 | (2006.01) |
| A61K 31/7068 | (2006.01) |
| A61K 31/708 | (2006.01) |
| A61K 39/12 | (2006.01) |
| A61K 39/39 | (2006.01) |
| A61K 45/06 | (2006.01) |
| A61K 47/34 | (2017.01) |
| A61P 35/00 | (2006.01) |
| A61K 39/00 | (2006.01) |

(52) U.S. Cl.

CPC .......... *A61K 31/454* (2013.01); *A61K 31/497* (2013.01); *A61K 31/675* (2013.01); *A61K 31/708* (2013.01); *A61K 39/12* (2013.01); *A61K 39/39* (2013.01); *A61K 45/06* (2013.01); *A61K 47/34* (2013.01); *A61N 5/1027* (2013.01); *A61P 35/00* (2018.01); *A61K 2039/525* (2013.01); *A61K 2039/53* (2013.01); *A61K 2039/55561* (2013.01); *A61K 2039/585* (2013.01); *A61N 2005/1024* (2013.01); *A61N 2005/1098* (2013.01)

(56) References Cited

U.S. PATENT DOCUMENTS

| | | | |
|---|---|---|---|
| 8,834,837 | B2 | 9/2014 | Kelson et al. |
| 9,642,817 | B2 | 5/2017 | Machluf et al. |
| 10,849,921 | B2 | 12/2020 | Quintero Ortiz et al. |
| 2002/0055667 | A1 | 5/2002 | Mavity et al. |
| 2004/0018968 | A1 | 1/2004 | Sgouros et al. |
| 2006/0223742 | A1 | 10/2006 | Salazar |
| 2007/0036764 | A1 | 2/2007 | Shir et al. |
| 2008/0124366 | A1 | 5/2008 | Ohlfest et al. |
| 2009/0088401 | A1 | 4/2009 | Salazar |
| 2009/0136422 | A1 | 5/2009 | Kelson et al. |
| 2009/0234628 | A1* | 9/2009 | Yu ..................... A61N 5/1031 |
| | | | 703/11 |
| 2010/0015042 | A1 | 1/2010 | Keisari et al. |
| 2011/0038888 | A1 | 2/2011 | Emtage |
| 2012/0164214 | A1 | 6/2012 | Machluf et al. |
| 2013/0011333 | A1 | 1/2013 | Yuan et al. |
| 2016/0108123 | A1* | 4/2016 | Freeman ............... A61K 45/06 |
| | | | 435/69.6 |
| 2016/0333355 | A1 | 11/2016 | Deng et al. |
| 2017/0224618 | A1 | 8/2017 | Machluf et al. |
| 2018/0126012 | A1 | 5/2018 | Weichert et al. |
| 2018/0214583 | A1 | 8/2018 | Scholz |
| 2018/0243444 | A1* | 8/2018 | Pozuelo Rubio ........ A61K 9/19 |
| 2018/0346596 | A1 | 12/2018 | Levitzki et al. |
| 2019/0083626 | A1* | 3/2019 | Goldberg ......... A61K 39/39541 |
| 2019/0292546 | A1* | 9/2019 | Lebecque ............... A61N 5/10 |
| 2020/0101079 | A1* | 4/2020 | Rudolph ............ A61K 31/5365 |
| 2020/0230248 | A1 | 7/2020 | Pombo-Villar et al. |
| 2020/0407453 | A1 | 12/2020 | Levitzki et al. |
| 2021/0100810 | A1* | 4/2021 | Klaus ................. A61K 31/4412 |
| 2021/0128945 | A1 | 5/2021 | Schmidt et al. |
| 2021/0130906 | A1* | 5/2021 | McGrail .......... G01N 33/57423 |
| 2021/0330807 | A1* | 10/2021 | Stark ...................... A61K 38/12 |

FOREIGN PATENT DOCUMENTS

| | | | |
|---|---|---|---|
| EP | 2379597 | B1 | 11/2016 |
| EP | 3319587 | B1 | 8/2019 |
| GB | 2555364 | A | 4/2018 |
| RU | 2284818 | C2 | 10/2006 |
| WO | 2001087313 | A1 | 11/2001 |
| WO | 2005013891 | A2 | 2/2005 |
| WO | 2006043083 | A2 | 4/2006 |
| WO | 2011088456 | A2 | 7/2011 |
| WO | 2011161075 | A1 | 12/2011 |
| WO | 2013106852 | A1 | 7/2013 |
| WO | 2017085228 | A1 | 5/2017 |
| WO | 2017173101 | A1 | 10/2017 |
| WO | 2018026884 | A1 | 2/2018 |
| WO | 2018207105 | A1 | 11/2018 |
| WO | 2019171308 | A1 | 9/2019 |
| WO | 2019193464 | A1 | 10/2019 |
| WO | 2020201568 | A1 | 10/2020 |

OTHER PUBLICATIONS

AU Application # 2019370892 Office Action dated Nov. 25, 2022.

EP Application # 19879337.4 Office Action dated Apr. 6, 2023.

CN Application # 2019800709663 Office Action dated Apr. 28, 2023.

Nakayama, "Antigen Presentation by MHC-Dressed Cells", Frontiers in Immunology, vol. 5, article 672, pp. 1-8, Jan. 5, 2015.

Keisari, "Tumor Abolition and Antitumor Immunostimulation by Physico-Chemical Tumor Ablation," Frontiers of Bioscience, vol. 22, pp. 310-347, January 217.

Papaioannou et al., "Harnessing the Immune System to Improve Cancer Therapy," Annals of Translational Medicine, vol. 4, No. 14, p. 1-15, Jul. 4, 2016.

Aznar et al. "Intratumoral Delivery of Immunotherapy—Act Locally, Think Globally," The Journal of Immunology, vol. 198, No. 1, pp. 31-39, year 2017.

Levitzki, "Targeting The Immune System To Fight Cancer Using Chemical Receptor Homing Vectors Carrying Polyinosine/Cytosine (PolyIC)," Frontiers in Oncology, vol. 2, No. 4, pp. 1-11, Feb. 8, 2012.

Lee et al., "Nanoparticle-Based Targeted Gene Therapy for Lung Cancer," American Journal of Cancer Research, vol. 6, No. 5, pp. 1118-1134, May 2016.

Langut et al., "PSMA-Homing dsRNA Chimeric Protein Vector Kills Prostate Cancer Cells and Activates Anti-Tumor Bystander Responses," Oncotarget, vol. 8, No. 15, pp. 24046-24062, Apr. 2017.

Duewell et al., "RIG-I-Like Helicases Induce Immunogenic Cell Death of Pancreatic Cancer Cells and Sensitize Tumors Toward Killing by CD8+ T Cells," Cell Death and Differentiation, vol. 21, No. 12, 1825-1837, year 2014.

Chiappinelli et al., "Inhibiting DNA Methylation Causes an Interferon Response in Cancer via dsRNA Including Endogenous Retroviruses," Cell, vol. 162, issue 5, pp. 974-986, Aug. 27, 2015.

InvivoGen "CDS Ligands", pp. 1-2, years 2011-2016.

InvivoGen, "Cyclic Dunecleotides and Xanthenon Derivative", pp. 1-3, years 2011-2016.

Vasir et al., "Biodegradable Nanoparticles for Cytosolic Delivery of Therapeutics," Advanced Drug Delivery Reviews, vol. 59, No. 8, pp. 718-728, Aug. 10, 2007.

Kalaydina et al., "Recent advances in "smart" delivery systems for extended drug release in cancer therapy," International Journal of Nanomedicine, vol. 13, pp. 4727-4745, year 2018.

Oronsky et al., "Turning on the Radio: Epigenetic Inhibitors as Potential Radiopriming Agents," Biomolecules, vol. 6, No. 32, pp. 1-13, Jul. 4, 2016.

Yoshida et al., "Toll-Like Receptor 3 Signal Augments Radiation-Induced Tumor Growth Retardation in a Murine Model," Cancer Science, vol. 109, pp. 956-965, Feb. 2018.

Confino et al., "Inhibition of Mouse Breast Adenocarcinoma Growth by Ablation with Intratumoral Alpha-Irradiation Combined with Inhibitors of Immunosuppression and CpG," Cancer Immunology, Immunotherapy, vol. 65, No. 10, pp. 1149-1158, Aug. 6, 2016.

International Application # PCT/IB2019/059331 dated Jan. 19, 2020.

InvivoGen, "RIG-I-Like Receptors & Cytosolic DNA Sensors", pp. 1-5, year 2012.

BIONCOTECH Therapeutics, "Clinical candidate BO-112: a nanomedicine capable of stimulating innate and adaptive immune responses and triggering apoptosis in cancer cells", pp. 1-16, Nov. 2016.

(56) References Cited

OTHER PUBLICATIONS

Garcia-Pascual et al., "Evaluation of the antiproliferative, proapoptotic, and antiangiogenic effects of a double-stranded RNA mimic complexed with polycations in an experimental mouse model of leiomyoma," Fertility and Sterility, vol. 105, No. 2, pp. 529-538, Feb. 2016.

Garcia-Pascual et al., "Evaluation of the potential therapeutic effects of a double-stranded RNA mimic complexed with polycations in an experimental mouse model of endometriosis," Fertility and Sterility, vol. 104, No. 5, pp. 1310-1318, Nov. 2015.

BIONCOTECH Therapeutics, "Exploratory Study of BO-112 in Adult Patients with Aggressive Solid Tumors," Trial Record 1 of 1 for BO-112, Cancer Spain, pp. 1-5, Jul. 11, 2016.

Edinger et al., "Targeting polyIC to EGFR over-expressing cells using a dsRNA binding protein domain tethered to EGF," PLOS one, pp. 1-17, Sep. 6, 2016.

Zigler et al., "HER2-Targeted Polyinosine/Polycytosine Therapy Inhibits Tumor Growth and Modulates the Tumor Immune Microenvironment," Cancer Immunology Research, vol. 4, No. 8, pp. 688-698, Aug. 2016.

Garrido et al., "The urgent need to recover MHC class I in cancers for effective immunotherapy," Current Opinion in Immunology, vol. 39, pp. 44-51, year 2016.

Baird et al., "Stimulating innate immunity to enhance radiation therapy-induced tumor control," International Journal of Radiation Oncology, Biology, Physics, vol. 99, No. 2, pp. 362-373, year 2017.

Confino et al., "Tumor ablation by intratumoral Ra-224-loaded wires induces anti-tumor immunity against experimental metastatic tumors," Cancer Immunology, Immunotherapy, vol. 64, No. 2, pp. 191-199, year 2015.

Langut et al., "PSMA-targeted polyinosine/polycytosine vector induces prostrate tumor regression and invokes an antitumor immune response in mice," Proceedings of the National Academy of Sciences of the United States of America (PNAS), vol. 114, No. 52, pp. 13655-13660, Dec. 26, 2017.

Shirota et al., "Intra-tumoral injection of CpG oligonucleotides induces the differentiation and reduces the immunosuppressive activity of myeloid-derived suppressor cells," The Journal of Immunology, vol. 188, No. 4, pp. 1592-1599, Feb. 15, 2012.

Wang et al., "Intratumoral injection of a CpG oligonucleotide reverts resistance to PD-1 blockade by expanding multifunctional DC8+ T cells," Proceedings of the National Academy of Sciences of the United States of America (PNAS), published online, pp. 1-10, Oct. 31, 2016.

Zhou et al., "TLR3 activaton efficiency by high or low molecular mass poly I:C," Innate Immunity, vol. 19, No. 2, pp. 184-192, year 2013.

Luo et al., "A STING-activating nanovaccine for cancer immunotherapy," Nature Nanotechnology, Letters, published online, pp. 1-10, Apr. 24, 2017.

Zeng et al., "Extracellular vesicle-mediated MHC cross-dressing in immune homeostasis, transplantation, infectious diseases, and cancer," Seminars in Immunopathology, Springer Natur, published online, pp. 1-14, Mar. 28, 2018.

Hammerich et al., "Systemic clinial tumor regressions and potentiation of PD1 blockade with in situ vaccination," online publication, www.nature.com/naturemedicine, Nature Medicine, pp. 1-23, May 2019.

Ma et al., "RIG-like Helicase Regulation of Chitinase 3-like 1 Axis on Pulmonary Metastasis," Scientific Reports, pp. 1-13, May 2016.

Radkewich-Brown et al., "Intratumoral DNA electroporation induces anti-tumor immunity and tumor regression," Author Manuscript, PubMed Central, National Institute of Health, pp. 1-17, Jul. 2013.

Marabelle et al., "Intratumoral Immunization: A New Paradigm for Cancer Therapy," Clinical Cancer Research, vol. 20, issue 7, pp. 1747-1756, Apr. 1, 2014.

Linehan et al., "A minimal RNA ligand for potent RIG-I activation in living mice," bioRxiv preprint, pp. 1-30, first posted online Aug. 19, 2017.

Aznar et al., "Immunotherapeutic effects of intratumoral nanoplexed poly I:C," Journal for ImmunoTherapy of Cancer, vol. 7, No. 116, pp. 1-16, year 2019.

Besch et al., "Proapoptotic signaling induced by RIG-I and MDA-5 results in type I interferon-independent apoptosis in human melanoma cells," The Journal of Clinical Investigation, vol. 119, No. 8, pp. 2399-2411, Aug. 2009.

Stone et al., "Nanoparticle-delivered multimeric soluble CD40L DNA combined with toll-like receptor agonists as a treatment for melanoma," PLoS ONE, vol. 4, issue 10, pp. 1-14, Oct. 2009.

Duewell et al., "Targeted activation of melanoma differentiation-associated protein 5 (MDA5) for immunotherapy of pancreatic carcinoma," OncoImmunology, vol. 4, No. 10, pp. 1-11, Oct. 2015.

Jiang et al., "Innate immune responses in human monocyte-derived dendritic cells are highly dependent on the size and the 5' phosphorylation of RNA molecules," The Journal on Immunology, published online, pp. 1-10, Jul. 8, 2011.

Fujimura et al., "Inhibitory effect of the polyinosinic-polycytidylic acid/cationic liposome on the progression of murine B16F10 melanoma," European Journal of Immunology, vol. 36, pp. 3371-3380, year 2006.

Bhoopathi et al., "Pancreatic cancer-specific cell death induced in vivo by cytoplasmic-delivered polyinosine-polycytidylic acid," Cancer Research, vol. 74, issue 21, pp. 6224-6235, Nov. 1, 2014.

Rosenblum et al., "Progress and challenges towards targeted delivery of cancer therapeutics," Review Article, Nature Communications, vol. 9, pp. 1-12, year 2018.

RU Application # 2021106341 Office Action dated Jul. 6, 2023.

Domankevich-Bachar et al., "Alpha Radiation-Based Ablation of Solid Tumors Acts as in situ Vaccination and Activates Anti-Tumor Immunity," Cancer Microenvironment, vol. 11, No. S1, p. S87, Jun. 1, 2018.

Wu et al., "Intraperitoneal Administration of poly(I:C) with Polyethylenimine Leads to Significant Antitumor Immunity Against Murine Ovarian Tumors," Cancer Immunology, Immunotherapy, Springer, Berlin, vol. 60, No. 8, pp. 1085-1096, Apr. 28, 2011.

Cohen et al., "Activation of Specific Anti-Tumor Immunity by Alpha Radiation Brachytherapy in Combination with Immuno-Manipulation," Poster Session Online, p. 1-1, Apr. 1, 2018 downloaded from https://www.postersessiononline.eu/173580348_eu/congresos/ESTRO37/aula/-PO_1033_ESTRO37.pdf.

Keisari et al., "Activation of Specific Anti-Tumor Immunity by Alpha Radiation based Brachytherapy and Immunotherapy," Database Embase, Elsevier Science Publishers, Amsterdam, pp. S580-S581, Apr. 1, 2018.

Anonymous et al., 33rd Annual Meeting & Pre-Conference Programs of the Society for Immunotherapy of Cancer (SITC 2018), Journal for ImmunoTherapy of Cancer, vol. 6, suppl. 1, pp. 207-398, year 2018.

Domankevich-Bachar et al., "Cure of Triple Negative Breast Cancer Bearing Mice by Intratumoral Diffusion of Alpha-Particle Emitting Atoms in Combination with Cytoplasmic Delivery of PolyIC in a Neoadjuvant Setting," International Journal of Radiation: Oncology, Biology, Physics, Pergamon Press, USA, vol. 105, No. 1, p. S126, Sep. 1, 2019.

Domankevich et al., "Combining Alpha Radiation-Based Brachytherapy with Immunomodulators Promotes Complete Tumor Regression in Mice via Tumor-Specific Long-Term Immune Response," Cancer Immunology Immunotherapy, Springer, Berlin/Heidelberg, vol. 68, No. 12, pp. 1949-1958, Oct. 22, 2019.

Domankevich et al., "RIG-1-Like Receptor Activation Synergizes with Intratumoral Alpha Radiation to Induce Pncreatic Tumor Rejection, Triple-Negative Breast Metastases Clearance, and Antitumor Immune Memory in Mice," Frontiers in Oncology, vol. 10, pp. 1-12, Jul. 17, 2020.

Keisari et al., "Immunostimulation and Decitabine can Augment Tumor Local Control and Anti-Tumor Immunity in Mice with Squamous Cell and Breast Cancer Treated by Alpha-Radiation," International Journal of Radiation: Oncology Biology Physics, Pergamon Press, USA, vol. 108, No. 3, p. e568, Nov. 1, 2020.

AU Application # 2019370892 Office Action dated Apr. 26, 2022.

EP Application # 19879337.4 Search Report dated Jun. 21, 2022.

IN Application # 202147023837 Office Action dated Jun. 29, 2022.

(56) References Cited

OTHER PUBLICATIONS

Wu et al., "Nanoparticle-Mediated Cytoplasmic Delivery of Messenger RNA Vaccines: Challenges and Future Perspectives," Parmaceutical Research, vol. 38, issue 3, pp. 473-478, year 2021.

Pardi et al., "mRNA Vaccines—a New Era in Vaccinology," Nature Reviews—Drug Discovery, vol. 17, issue 4, pp. 261-279, Apr. 2018.

AU Application # 2019370892 Office Action dated Jan. 27, 2023.

RU Application # 2021106341 Office Action dated Feb. 13, 2023.

AU Application # 2019370892 Office Action dated Mar. 22, 2023.

Duan et al., "Toll-Like Receptor Signaling and its Role in Cell-Mediated Immunity," Frontiers in Immunology, vol. 13, pp. 1-22, Mar. 2022.

Qiu et al., "DNA Methyltransferase Inhibitor 5-aza-CdR Enhances the Radiosensitivity of Gastric Cancer Cells," Cancer Science, vol. 100, No. 1, pp. 181-188, year 2009.

Oshima et al., "Immunomodulatory Drugs (IMiDs)," Abstract, Nippon Rinsho, vol. 72, No. 6, pp. 1130-1135, year 2014.

Kobiyama et al., "Development Nucleic Acid-Based Adjuvant for Cancer Immunotherapy," abstract, Japanese Journal of Cancer and Chemotherapy, vol. 42, No. 9, pp. 1040-1045, Sep. 2015.

Fujiwara, "Radiosensitization by Telomerase-Specific Oncolytic Virotheraphy," abstract, Japanese Journal of Clinical Oncology, vol. 55, No. 12, pp. 874-879, year 2009.

Levitzki, "Targeting the Immune System to Fight Cancer Using Chemical Receptor Homing Vectors Carrying Polyinosine/Cytosine (PolyIC)," Frontiers in Oncology, vol. 2, article 4, pp. 1-10, Feb. 2012.

Arazi et al., "Treatment of Solid Tumors by Interstitial Release of Recoiling Short-Lived Alpha Emitters," Physics in Medicine and Biology, vol. 52, No. 16, pp. 5025-5042, year 2007.

Prokofieva, "Dosing of Medicinal Substances; General Rules for Dosing of Medicinal Substances", Course of lectures on general pharmacology/Training manual, Ulyanovsk, Russia, pp. 11-12, year 2017.

Perevodchikova, "General Information about Clinical Chemotherapy," Chapter 1, Practical medicine, pp. 21-25, year 2011.

Belikov, "Pharmaceutical Chemistry", chapter 2.2 Relationship Between the Structure of Molecules of Substances and their Effect on the Body, pp. 1-3, year 1993.

Litvinenko, "Action of Ionizing Radiation on Tumor", Science, technology and education, vol. 1, pp. 113-114, year 2014.

EP Application # 19879337.4 Office Action dated Nov. 10, 2023.

RU Application 2021106341 Office Action dated Dec. 1, 2023.

JP Application # 2021518633 Office Action dated Dec. 5, 2023.

EP Application # 19879337.4 Office Action dated May 29, 2024.

JP Application # 2021518633 Office Action dated May 31, 2024.

AU Application # 2023208136 Office Action dated Jul. 5, 2024.

Thangamathesvaran et al., "Immune Checkpoint Inhibitors and Radiotherapy—Concept and Review of Current Literature," Annals of Translational Medicine, vol. 6, issue 8, article 155, pp. 1-11, Mar. 9, 2018.

O'Cathail et al., "Combining Oncolytic Adenovirus with Radiation—a Pardigm for the Future of Radiosensitization," Frontiers in Oncology, vol. 7, article 153, pp. 1-13, Jul. 2017.

Talamo et al., "Current Role of Radiation Therapy for Multiple Myeloma," Frontiers in Oncology, vol. 5, No. 40, pp. 1-6, Feb. 18, 2015.

Butowski et al., "A Phase II Clinical Trial of Poly-ICLC with Radiation for Adult Patients with Newly Diagnosed Supratentorial Glioblastome: A North American Brain Tumor Consortium (NABTC01-05," Journal of Neuro-Oncology, vol. 91, No. 2, pp. 175-182, Jan. 2009.

"8th International Conference on Tumor Microenvironment—Progression, Therapy and Prevention—Program and Abstracts," The International Cancer Microenvironment Society, vol. 11, suppl. 1, pp.s S1-91, Jun. 14, 2018.

KR Application # 1020217013680 Office Action dated Sep. 12, 2024.

AU Application # 2023208136 Office Action dated Feb. 18, 2025.

* cited by examiner

1

INTRATUMORAL ALPHA-EMITTER RADIATION AND ACTIVATION OF CYTOPLASMATIC SENSORS FOR INTRACELLULAR PATHOGEN

FIELD OF THE INVENTION

The present invention relates generally to tumor therapy and particularly to combined intratumoral alpha-emitter radiation and activation of cytoplasmatic sensors for intracellular pathogen (hereafter, "ACSIP").

BACKGROUND OF THE INVENTION

Cancer is the primary cause of death in many countries around the world. Accordingly, an enormous amount of resources has been spent on treatments for cancer and other tumors, and a wide variety of such treatments have been suggested.

One class of tumor therapy is tumor ablation, to kill tumor cells in situ. In addition to killing cells in situ, in some cases, ablation induces an anti-tumoral immune response for the elimination of residual and distant tumor cells. This happens due to the dispersion of tumoral antigens and danger signals that are released from dead and/or dying tumor cells. Tumoral antigens are captured by antigen-presenting cells that in turn present those to T-cells, for example, via a cross presentation pathway as described in Nakayama, Masafumi. "Antigen presentation by MHC-dressed cells." *Frontiers in immunology* 5 (2015): 672.

Multiple ablation methods have been proposed, such as, heat, microwave, laser, electric, photodynamic, chemical (e.g., using reactive oxygen species (ROS)) and radioactive ablation, which could be applied externally (e.g., external beam radiation therapy) or internally (e.g., brachytherapy), and can include different types of radiation such as alpha radiation, beta radiation and gamma radiation. A discussion of these methods appears, for example, in Keisari, Yona. "Tumor abolition and antitumor immunostimulation by physico-chemical tumor ablation." *Front Biosci* 22 (2017): 310-347. The ablation method used for any specific patient is generally selected according to the type of the tumor, its location, its stage and/or other parameters of the tumor.

Another class of tumor therapy, referred to as immuno-therapy, involves the enhancement of a patient's immune response against tumor cells. Many immunotherapy methods have been suggested, such as: checkpoint inhibitors, Toll-like receptor (TLR) agonists (e.g. CpG), local gene therapy, cytokine therapy, antibodies against certain protein targets, CAR-T cell therapy, dendritic cell vaccine, adoptive transfer of tumor infiltrating lymphocytes and oncolytic virotherapy. These methods are discussed, for example, in Papaioannou, Nikos E., et al. "Harnessing the immune system to improve cancer therapy." *Annals of translational medicine* 4.14 (2016). Immunotherapy strategies may include local therapies as described in Aznar, M. Angela, et al. "Intratumoral delivery of immunotherapy act locally, think globally." *The Journal of Immunology* 198.1 (2017): 31-39. Generally, the specific method used for each patient is selected according to the type of the tumor or its stage. Multiple combinations of the above discussed therapy types were tested in pre-clinical and clinical trials, as described, for example, in Table 1 of the above-mentioned article of Aznar.

US patent publication 2009/0088401 to Salazar describes an autovaccination method consisting of induction of an immunogenic cell death in one or more targeted tumor sites followed by injection of dsRNAs in the same tumor site.

SUMMARY OF THE INVENTION

An aspect of some embodiments of the invention relates to tumor treatment based on a synergy between activation of cytoplasmatic sensors for intracellular pathogens (ACSIP) and intra-tumoral alpha-emitter radiotherapy.

There is provided in accordance with embodiments of the invention, a method of treating a patient with a tumor, comprising administering, to the patient, a substance which activates cytoplasmatic sensors for intracellular pathogen in the tumor and treating the tumor with intra-tumoral alpha-emitter radiotherapy within two weeks of administering the substance which activates cytoplasmatic sensors for intracellular pathogen in the tumor.

Optionally, administering the substance comprises administering an agent which induces production within the cell of molecules, which stimulate cytoplasmatic sensors for an intracellular pathogen. Optionally, the agent comprises a DNA methyltransferase (DNMT) inhibitor, such as Decitabine, Azacytidine and/or Guadecitabine. Alternatively or additionally, administering the agent comprises administering a histone deacetylase (HDAC) inhibitor, such as Entinostat and/or vorinostat. Optionally, administering the substance comprises administering a pathogen mimic with a delivery agent suitable for cytoplasmic delivery of the pathogen mimic. Optionally, administering the pathogen mimic together with a delivery agent comprises administering a single dose of the intracellular pathogen mimic in a single session or two doses. In some embodiments, administering the pathogen mimic together with a delivery agent comprises administering at least three doses of the intracellular pathogen mimic in respective separate sessions. Optionally, administering the substance comprises administering the substance with a delivery agent suitable for Targeted delivery. Optionally, the delivery agent comprises a lipid based delivery agent, a polymer based delivery agent, a cationic polymer complex, a cationic lipid, a liposome, a lipoplex, a polymeric micelles and/or a dendrimer. Alternatively or additionally, the delivery agent comprises a solid nanoparticle, such as a solid lipid nanoparticle and/or a solid polymeric nanoparticle. Further alternatively or additionally, the delivery agent comprises a metal-based nanoparticle system. In some embodiments, the delivery agent comprises polyethylenimine (PEI).

In some embodiments, administering the pathogen mimic comprises administering a bacteria mimic and/or a viral mimic. Optionally, administering the viral mimic comprises administering double stranded RNA (dsRNA). Optionally, administering the dsRNA comprises administering polyIC. In some embodiments, the polyIC is delivered with polyethylenimine (PEI), for example by administering BO-112. Alternatively or additionally, the dsRNA comprises 5' ppp-dsRNA, 3p-hpRNA, Poly(dA:dT), poly-ICLC, poly(A:U) and/or CpG rich RNA. Optionally, administering the pathogen mimic comprises administering a pathogen mimic that is recognized by intracellular receptors as non-self. Optionally, administering the substance which activates cytoplasmatic sensors for intracellular pathogen comprises administering a plurality of different substances which activate cytoplasmatic sensors for intracellular pathogen.

Optionally, administering a plurality of different substances which activate cytoplasmatic sensors for intracellular pathogen comprises administering a first agent which induces production within the cell of molecules, which stimulate cytoplasmatic sensors for an intracellular pathogen and a second agent comprising a pathogen mimic with a delivery agent suitable for cytoplasmic delivery of the pathogen mimic. Optionally, the method includes additionally administering to the patient a supportive treatment of cyclophosphamide. Optionally, treating the tumor with alpha-emitter radiotherapy comprises inserting a brachytherapy source carrying alpha-emitting radionuclides into the tumor. Optionally, the brachytherapy source releases alpha-emitting radionuclides at a rate of less than 25% of the alpha-emitting radionuclides on the source when inserted to the tumor, per day. Optionally, the brachytherapy source comprises a Radium source. Optionally, treating the tumor with alpha-emitter radiotherapy is performed only after completing the administering of the substance. Optionally, administering the substance comprises administering with nanoghosts, which direct the substance to the tumor. Optionally, administering the substance comprises administering one or more substances in at least two separate sessions separated from each other by at least 12 hours. Optionally, administering the one or more substances comprises administering in at least three separate sessions separated from each other by at least 20 hours. Optionally, the method includes identifying a primary tumor in the patient and wherein administering the substance comprises administering the substance to the identified primary tumor. Optionally, treating the tumor with alpha-emitter radiotherapy comprises treating with alpha-emitter radiotherapy less than 80 hours after administering a last dose of the substance. Optionally, treating the tumor with alpha-emitter radiotherapy comprises treating with alpha-emitter radiotherapy less than 60 hours after administering a last dose of the substance. Optionally, treating the tumor with alpha-emitter radiotherapy comprises treating with alpha-emitter radiotherapy at least 12 hours or 24 hours after administering a last dose of the substance.

Optionally, the method includes additionally administering to the patient a supportive treatment which counters accelerated tissue repair induced by the alpha-emitter radiotherapy, such as a supportive treatment which downregulates inflammation and/or a supportive treatment which downregulates checkpoint expression. In some embodiments, the supportive treatment includes cyclophosphamide, pomalidomide and/or berzosertib. Alternatively or additionally, the supportive treatment includes a checkpoint blockade. Optionally, the supportive treatment includes anti-PD-1, anti-PD-L1 and/or anti-CTLA4. In some embodiments, the supportive treatment includes one or more TLR agonists, one or more MSDCs inhibitors, one or more Tregs inhibitors, one or more DNA repair inhibitors and/or one or more Antiangiogenic factors. In some embodiments, the method includes performing surgery to remove the tumor, at least a week after beginning treating the tumor with alpha-emitter radiotherapy. Optionally, treating the tumor with intra-tumoral alpha-emitter radiotherapy comprises treating the tumor with intra-tumoral alpha-emitter radiotherapy less than a week after administering the substance which activates cytoplasmatic sensors for intracellular pathogen in the tumor.

There is further provided in accordance with an embodiment of the present invention, a kit for treatment of a patient, comprising at least one source for being at least partially introduced into a body of a subject, having alpha-emitting atoms mounted thereon, at least one substance which activates cytoplasmatic sensors for intracellular pathogen; and a sterile package containing the at least one source and the at least one substance.

Optionally, the alpha-emitting atoms are mounted on the source in a manner which allows controllable release of the alpha-emitting atoms or their daughter radionuclides from the source. Optionally, the alpha-emitting atoms comprise radium atoms. Optionally, the at least one substance comprises a DNA methyltransferase (DNMT) inhibitor. Optionally, the DNA methyltransferase (DNMT) inhibitor comprises Decitabine. Optionally, the at least one substance further comprises a pathogen mimic with a delivery agent suitable for cytoplasmic delivery of the pathogen mimic. Optionally, the at least one substance comprises a pathogen mimic with a delivery agent suitable for cytoplasmic delivery of the pathogen mimic. Optionally, the kit includes in the sterile package, a supportive treatment drug which counters accelerated tissue repair induced by the alpha-emitter radiotherapy. Optionally, the supportive treatment drug comprises a drug which downregulates inflammation.

There is further provided in accordance with embodiments of the present invention, use of $polyIC^{PEI}$ in the production of a medicament for administering to a tumor of a patient wherein the administration pattern of the medicament comprises administering a therapeutically effective amount of $polyIC^{PEI}$ to the tumor, in one or more sessions, followed by treating the tumor with intra-tumoral alpha-emitter radiotherapy less than a week after administering the $polyIC^{PEI}$.

There is further provided in accordance with embodiments of the present invention, use of a DNA methyltransferase (DNMT) inhibitor in the production of a medicament for administering to a tumor of a patient wherein the administration pattern of the medicament comprises administering a therapeutically effective amount of the DNMT inhibitor.

The various options and alternatives listed above may be used in the alternative or together in any suitable combination, except where the options are specifically contradictory.

DETAILED DESCRIPTION OF EMBODIMENTS

Figure 1:
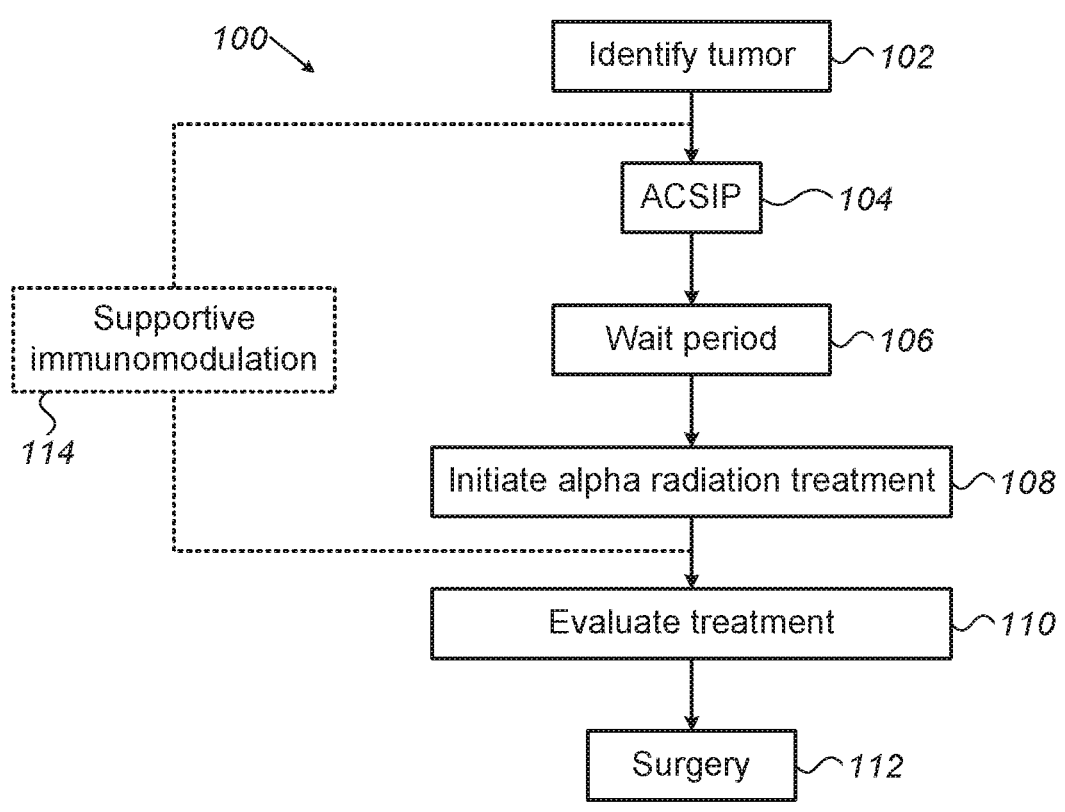
FIG. 1 is a flowchart of a therapy method, in accordance with an embodiment of the invention.

An aspect of some embodiments of the invention relates to a combined tumor treatment including activation of cytoplasmatic sensors for intracellular pathogens (ACSIP) in a tumor in a patient and applying alpha-emitter radiation to the tumor 12-90 hours after a treatment inducing ACSIP. Applicant has found that the combination of the specific immunotherapy of inducing ACSIP followed by the specific tumor ablation of applying alpha-emitter radiation has a substantially greater therapeutic effect than each of the treatments separately.

It is believed by applicant that ACSIP, which increases the expression of MHC1 molecules on tumor cells, also increases the probability of the presentation of yet-unpresented tumor antigens by tumor cells prior to the cell death induced by intra-tumoral alpha-emitter radiation. The induction of tumor cell death by alpha-emitter radiation following the presentation of a wider range of tumor antigens, in its turn, will promote the recruitment and activation of antigen presenting cells, by releasing Damage-associated molecular patterns (DAMP) signals. Since antigen presenting cells activate specific T-cell responses, more antigen-specific T cells would be activated to recognize a wider range of tumor antigens, leading to a stronger and long lasting systemic- and specific-adaptive immune response against a wider range of tumor antigens. In addition, the killing of tumor cells containing factors, which induce ACSIP will also lead to the release of pathogen-associated molecular patterns (PAMPs), and cytokines to enhance the recruitment and activation of the immune response. Together, the alpha-emitter radiation and ACSIP induction may generate a snowball effect which increases the killing of tumor cells, which increases the immune response, which still further increases the killing of tumor cells and so on. It is possible that the positive results of combining alpha-emitter radiotherapy with ACSIP is due to the slow release of the alpha-emitting atoms, which distributes the effect of the radiotherapy over time and achieves the synergy with the ACSIP. The ACSIP provided before the radiotherapy may decondense the DNA of the tumor cells and cause the tumor cells to be more sensitive to the radiotherapy. Thus, the combined alpha-emitter radiation and inducement of ACSIP leads to a significant local and systemic tumor killing, at a minimal period with minimal adverse effects and increased efficiency.

The induction of ACSIP is performed, in some embodiments, by administering a pathogen mimic into the cytoplasm of the tumor cells using a delivery agent suitable for cytoplasmatic delivery. Alternatively to cytoplasmatic administration of a pathogen mimic, the ACSIP induction is achieved by stimulating an endogenous intracellular pathogen and/or by activating promoters of cytoplasmatic pathogen sensors of the cells of the tumor, for example by administering a DNA methyltransferase (DNMT) inhibitor, such as Decitabine.

Treatment Method

FIG. 1 is a flowchart of a therapy method 100, in accordance with an embodiment of the invention. Further to identification (102) of a tumor in a patient, therapy method 100 begins with inducing (104) ACSIP in the patient in one or more sessions. A limited time period (106) after the ACSIP induction (104), an alpha-emitter radiation treatment (referred to herein also as alpha-emitter radiotherapy) of the tumor is initiated (108).

In some embodiments, one or more supportive immunomodulatory treatments, are provided (114) before and/or during induction of ACSIP, while the alpha-emitter radiation treatment is provided and/or after the alpha-emitter radiation treatment is completed. In some embodiments, after the alpha-emitter radiation treatment is completed, the effect of the treatment is evaluated (110). In some embodiments, following evaluation, a surgery (112) to remove the residual primary tumor is employed. In some embodiments, the surgery is carried out at least a week or even at least 14 days following the beginning or completion of the radiation treatment. While surgery to remove a cancerous tumor is generally performed as soon as possible, applicant has found that after applying a combined ACSIP and radiotherapy treatment it is better to wait in order to allow the treatment to take effect and only then to remove the tumor. Alternatively surgery is performed at any other suitable time or is not performed at all, when deemed unnecessary or unfeasible. Further alternatively or additionally, the evaluation is not performed.

Tumor Types

Therapy method 100 may be used in treatment of any tumor type, including cancerous tumors, benign neoplasms, in situ neoplasms (pre malignant), malignant neoplasms (cancer), and neoplasms of uncertain or unknown behavior. In some embodiments, the method of FIG. 1 is used to treat relatively solid tumors, such as breast, kidney, pancreatic, skin, head and neck, colon, ovarian, bladder, and prostate cancer. In other embodiments, the method of FIG. 1 is used to treat non-solid tumors. The method of FIG. 1 may be used for both primary and secondary growths.

Exemplary tumors that can be treated by the method of FIG. 1 include tumors of the gastrointestinal tract (colon carcinoma, rectal carcinoma, colorectal carcinoma, colorectal cancer, colorectal adenoma, hereditary nonpolyposis type 1, hereditary nonpolyposis type 2, hereditary nonpolyposis type 3, hereditary nonpolyposis type 6; colorectal cancer, hereditary nonpolyposis type 7, small and/or large bowel carcinoma, esophageal carcinoma, tylosis with esophageal cancer, stomach carcinoma, pancreatic carcinoma, pancreatic endocrine tumors), endometrial carcinoma, dermatofibrosarcoma protuberans, gallbladder carcinoma, Biliary tract tumors, prostate cancer, prostate adenocarcinoma, renal cancer (e.g., Wilms' tumor type 2 or type 1), liver cancer (e.g., hepatoblastoma, hepatocellular carcinoma, hepatocellular cancer), bladder cancer, embryonal rhabdomyosarcoma, germ cell tumor, trophoblastic tumor, testicular germ cells tumor, immature teratoma of ovary, uterine, epithelial ovarian, sacrococcygeal tumor, choriocarcinoma, placental site trophoblastic tumor, epithelial adult tumor, ovarian carcinoma, serous ovarian cancer, ovarian sex cord tumors, cervical carcinoma, uterine cervix carcinoma, small-cell and non-small cell lung carcinoma, nasopharyngeal, breast carcinoma (e.g., ductal breast cancer, invasive intraductal breast cancer; breast cancer, susceptibility to breast cancer, type 4 breast cancer, breast cancer-1, breast cancer-3; breast-ovarian cancer), squamous cell carcinoma (e.g., in head and neck), neurogenic tumor, astrocytoma, ganglioblastoma, neuroblastoma, gliomas, adenocarcinoma, adrenal tumor, hereditary adrenocortical carcinoma, brain malignancy (tumor), various other carcinomas (e.g., bronchogenic large cell, ductal, Ehrlich-Lettre ascites, epidermoid, large cell, Lewis lung, medullary, mucoepidermoid, oat cell, small cell, spindle cell, spinocellular, transitional cell, undifferentiated, carcinosarcoma, choriocarcinoma, cystadenocarcinoma), ependymoblastoma, epithelioma, erythroleukemia (e.g., Friend, lymphoblast), fibrosarcoma, giant cell tumor, glial tumor, glioblastoma (e.g., multiforme, astrocytoma), glioma, hepatoma, heterohybridoma, heteromyeloma, histiocytoma, hybridoma (e.g., B cell), hypernephroma, insulinoma, islet tumor, keratoma, leiomyoblastoma, leiomyosarcoma, lymphosarcoma, melanoma, mammary tumor, mastocytoma, medulloblastoma, mesothelioma, metastatic tumor, monocyte tumor, multiple myeloma, myelodysplastic syndrome, myeloma, nephroblastoma, nervous tissue glial tumor, nervous tissue neuronal tumor, neurinoma, neuroblastoma, oligodendroglioma, osteochondroma, osteomyeloma, osteosarcoma (e.g., Ewing's), papilloma, transitional cell carcinoma, pheochromocytoma, pituitary tumor (invasive), plasmacytoma, retinoblastoma, rhabdomyosarcoma, sarcoma (e.g., Ewing's, histiocytic cell, Jensen, osteogenic, reticulum cell), schwannoma, subcutaneous tumor, teratocarcinoma (e.g., pluripotent), teratoma, testicular tumor, thymoma and trichoepitelioma, gastric cancer, fibrosarcoma, glioblastoma multiforme; multiple *glomus* tumors, Li-Frau-meni syndrome, liposarcoma, lynch cancer family syndrome II, male germ cell tumor, medullary thyroid, multiple meningioma, endocrine neoplasia, myxosarcoma, paraganglioma, familial nonchromaffin, pilomatricoma, papillary, familial and sporadic, rhabdoid predisposition syndrome, familial, rhabdoid tumors, soft tissue sarcoma, and Turcot syndrome with glioblastoma.

In some embodiments, the method of FIG. 1 is applied to a tumor known to be affected substantially by alpha-emitter radiation on its own. In other embodiments, the method of FIG. 1 is applied to a tumor of a type which is not affected substantially by alpha-emitter radiation on its own, for example does not reduce in size at all or does not reduce in size by more than 5% or 10%. Experiments performed by applicant indicate that even tumors that are not affected substantially by alpha-emitter radiation or ACSIP on their own reduce dramatically in size when targeted by the combination of ACSIP and alpha-emitter radiation in accordance with the method of FIG. 1.

Pathogen Mimic

In some embodiments, induction of ACSIP (104) is performed by delivering a pathogen mimic to the tumor cells. The delivered pathogen mimic includes, in some embodiments, a viral mimic. In other embodiments, an intracellular bacterial mimic is delivered into the tumor cells, instead of, or in addition to, a viral mimic. In some embodiments, the pathogen mimic comprises an intracellular pathogen mimic that is recognized by intracellular receptors as non-self.

In embodiments in which the pathogen mimic comprises a viral mimic, the viral mimic may include a DNA viral mimic or an RNA viral mimic, such as an ssRNA viral mimic or a dsRNA viral mimic. The dsRNA optionally includes a RIG-I-like Receptor (RLR) agonists, such as a Polyinosinic:polycytidylic acid (polyIC) molecule, for example as described in PCT publication WO 2017/085228, titled: "Novel Pharmaceutical Composition Comprising Particles Comprising A Complex Of A Double-Stranded Polyribonucleotide And A Polyalkyleneimine".

In some embodiments, the polyIC has a high molecular weight (HMW), for example a molecular weight above 1.2 kb, above 1.5 kb, above 2.5 kb or even above 4 kb. It is noted however, that the polyIC viral mimic may also include a low molecular weight (LMW) polyIC, of a molecular weight below 1 kb or even below 0.8 kb. Optionally, the molecular weight of the polyIC is selected according to the type of the tumor.

Alternatively, any of the other viral mimics described in PCT publication WO 2017/085228, which is incorporated herein by reference, may be used. In other embodiments, the delivered viral mimic comprises any other suitable viral mimic, such as one or more of 5' triphosphate double stranded RNA (5' ppp-dsRNA), 5' triphosphate hairpin RNA (3p-hpRNA) and/or Poly(dA:dT), poly-ICLC, poly(A:U), and/or CpG rich RNA.

In other embodiments, a DNA viral mimic comprising CDS or STING ligands, for example any of those listed in https://www.invivogen.com/dsdna and/or https://www.invivogen.com/cyclic-dinucleotide, which are incorporated herein by reference, are used. In one embodiment, a CpG ODN viral mimic is used.

Use of an RNA mimic has the advantage of having the ACSIP induction (104) operate through a different pathway than the alpha-emitter radiotherapy, which generally targets the DNA of cells.

Alternatively or additionally to using a pathogen mimic to induce ACSIP, an oncolytic virus is used for ACSIP induction.

Route of Administration

In some embodiments, identification (102) of the tumor comprises identification of one or more main tumors, for example a primary cancerous tumor and/or one or more secondary and/or metastases. The delivery (104) is performed in situ, by direct intra-tumoral injection to the one or more identified tumors.

In other embodiments, the delivery to the tumor and/or to metastases is done by systemic administration, using any suitable method of targeted delivery, for example using delivery by nanoghosts, such as described in US patent publication 2017/0224618 to Machluf et al., titled: "Liposomal Compositions and uses of same", which is incorporated herein by reference. Optionally, the pathogen mimic is delivered with a specific tumor marker which targets the tumor, so that the tumor marker together with the mimic, attaches to the tumor cells. The targeting is performed, for example as described in US patent publication 2018/0346596, titled: "Chimeric Proteins for targeting DSRNA" or in Alexander Levitzki, "Targeting The Immune System To Fight Cancer Using Chemical Receptor Homing Vectors Carrying Polyinosine/Cytosine (PolyIC)", frontiers in Oncology, 2012, the disclosures of which are incorporated herein by reference.

Optionally, before administering the pathogen mimic to a patient, a size of the tumor, tumors and/or metastases is estimated and accordingly an amount of the pathogen mimic to be administered is selected.

Delivery

In some embodiments, the pathogen mimic is administered to the patient along with a delivery agent (e.g., a reagent) which leads the pathogen mimic into the cells of the tumor. Optionally, the delivery agent is one that is able to by-pass membranal and/or endosomal receptors, such as the endosome/TL3 receptor. Optionally, the pathogen mimic and the delivery agent are administered as a single dose together. Optionally, the delivery agent encapsulates and/or is complexed with the pathogen mimic. For example, in one specific embodiment, a high molecular weight polyIC pathogen mimic is incubated with Polyethylenimine (PEI) in a ratio of Nucleic acid/Polymer between 6 and 8, to form a complex, hereafter termed polyIC$^{PEI}$. In another embodiment, BO-112 as described in PCT publication WO 2017/085228, is used. This complex is injected intratumorally in a dose of 20-70 mg polyIC (depending on tumor volume).

Optionally, the delivery agent comprises Polyethylenimine (PEI). Alternatively, the delivery agent is lipid-based, polymer-based or based on any other suitable nanoparticles, for example as described in Lee, Hung-Yen, Kamal A. Mohammed, and Najmunnisa Nasreen. "Nanoparticle-based targeted gene therapy for lung cancer." *American journal of cancer research* 6.5 (2016): 1118, the disclosure of which is incorporated herein by reference. In some embodiments, the delivery agent comprises a cationic polymer complex or a cationic lipid. Alternatively or additionally, the delivery agent comprises a liposome, a lipoplex, a dendrimer or a polymeric micelles. Further alternatively or additionally, the delivery agent comprises a solid nanoparticle, such as a solid lipid nanoparticle or a solid polymeric nanoparticle. In some embodiments, the delivery agent comprises a metal-based nanoparticle system.

The delivery is performed using any suitable method known in the art, such as any of the methods described in Langut, Yael, et al. "PSMA-homing dsRNA chimeric protein vector kills prostate cancer cells and activates anti-tumor bystander responses." *Oncotarget* 8.15 (2017): 24046 and/or in Duewell, P., et al. "RIG-I-like helicases induce immunogenic cell death of pancreatic cancer cells and sensitize tumors toward killing by CD8+ T cells." *Cell death*

*and differentiation* 21.12 (2014): 1825, the disclosures of which are incorporated herein by reference.

Stimulation of Endogenous Pathogens

In some embodiments, the ACSIP is induced (104) by stimulating in the tumor cells epigenetic changes, for example by stimulating an endogenous pathogen, such as endogenous retroviruses and/or by stimulating the activation of cytoplasmatic pathogen sensors by epigenetic changes, which activates the promoters of these sensors. The epigenetic changes are induced by an epigenetic agent. In some embodiments, the epigenetic agent comprises a DNA methyltransferase (DNMT) inhibitor, such as Decitabine, azacytidine and/or Guadecitabine. The stimulation is performed using any suitable method known in the art, such as any of the methods described in Chiappinelli et al., "Inhibiting DNA Methylation Causes an Interferon Response in Cancer via dsRNA Including Endogenous Retroviruses", Cell, Volume 162, Issue 5, Aug. 27, 2015, available from https:// www.cell.com/cell/fulltext/S0092-8674(15)00848-X, the disclosure of which is incorporated herein by reference in its entirety. In other embodiments, the epigenetic agent comprises a histone deacetylase (HDAC) inhibitor, such as Entinostat or vorinostat.

Optionally, the epigenetic agent is administered systemically. In other embodiments, the epigenetic agent is administered using targeted delivery, for example using nanoghosts, which directs the epigenetic agent to the tumor and possibly also to metastases. Further alternatively, the epigenetic agent is delivered locally by direct injection into a targeted tumor.

Multiple Treatment Sessions

In some embodiments, the ACSIP induction (104) is performed once before the alpha-emitter radiotherapy, in a single session. Alternatively, the ACSIP induction (104) is performed in multiple sessions, possibly at least two, at least three or even at least four sessions, separated by at least 24 hours. The limited time period (106) after the ACSIP induction (104) is counted, in accordance with this alternative, from the last ACSIP induction session. The multiple sessions optionally use the same ACSIP induction method. Alternatively, different sessions use different ACSIP induction methods. In still other embodiments, two or more ACSIP induction are performed in a same session concurrently or within less than an hour from each other.

One embodiment found to provide particularly promising results included a first ACSIP induction session of stimulating in the tumor cells epigenetic changes, a second session, 24 hours later, of both stimulating in the tumor cells epigenetic changes and delivering a pathogen mimic, a third session, 24 hours after the second session, including stimulating in the tumor cells epigenetic changes, and a fourth session, 24 hours after the third session, of both stimulating in the tumor cells epigenetic changes and delivering a pathogen mimic.

In one particular implementation of this embodiment, the ACSIP induction (104) includes 4 sessions based on Decitabine, every 24 hours, prior to alpha-emitter radiation, in combination with 2 doses of PolyIC with or without PEI, 72 and 24 hours prior to alpha-emitter radiation with one of the above listed delivery agents. The alpha-emitter radiation is optionally activated 1 day after the last session.

Alpha-Emitter Radiation

The alpha-emitter radiation treatment optionally includes brachytherapy, by insertion of seeds carrying alpha emitting atoms, such as Radium-224 or Radium-223, into the tumor. Optionally, the alpha emitting atoms are attached to the seed in a manner that the atoms do not leave the seed, but upon radionuclide decay resulting daughter radionuclides leave the seed. The brachytherapy seed optionally emits daughter radionuclide atoms at a rate of at least 0.1%, 0.5% or even at least 1% of the number of radionuclide atoms coupled to the seed when originally employed, per 24 hours. In some embodiments, the daughter radionuclide atoms are slowly released from the seed, at a rate of less than 25%, less than 10%, less than 5% or even less than 3% of the radionuclide atoms coupled to the seed, per 24 hours.

Alternatively to attaching the alpha emitting atoms to the seed in a manner that the atoms do not leave the seed without radionuclide decay, the alpha emitting atoms are attached to the seed in a manner that the atoms controllably leave the seed at a rate of at least 0.1% per 24 hours, in methods other than radionuclide decay, as described, for example in PCT publication WO 2019/193464, titled "controlled release of radionuclides", which is incorporated herein by reference.

In some embodiments, the alpha-emitter radiation comprises diffusing alpha-emitter radiation therapy (DaRT). The alpha-emitter radiotherapy is optionally carried out using any of the methods and/or devices described in U.S. Pat. No. 8,834,837, US patent publication 2009/0136422, U.S. provisional application 62/913,184, filed Oct. 10, 2019, and/or PCT publication WO 2018/207105, which are incorporated herein by reference.

The alpha-emitter radiation treatment is optionally initiated (108) by inserting one or more brachytherapy seeds comprising alpha emitting atoms on an outer surface of the seeds, into the tumor. Alternatively, the alpha-emitter radiotherapy is initiated by activating previously inserted seeds, carrying alpha emitting atoms. Optionally, in accordance with this alternative, the seeds are inserted into the patient with a bio-absorbable coating, which prevents alpha-radiation and/or the daughter radionuclides from leaving the seeds. The bio-absorbable coating optionally comprises polylactide (PLA), polyglycolide (PGA) or co-polymers of PLA and PGA, tailored to achieve a desired resorption rate of the coating. Alternatively or additionally, the coating comprises co-poly lactic acid/glycolic acid (PLGA). The polymers of the coating optionally have molecular weights ranging from 5,000 to 100,000. The material of the coating dissolves in the patient through any of the methods known in the art, such as one or more of ultrasonic energy, reaction with body temperature and/or reaction with body fluids. Additional discussion of bio-absorbable polymers which may be used in accordance with embodiments of the present invention after adjustment for the desired resorption rate are described in U.S. Pat. No. 8,821,364 and US patent publication 2002/0055667, which are incorporated herein by reference. In some embodiments, the initiation (108) includes applying a stimulus which dissolves the coating and thus allows the alpha radiation and/or the daughter radionuclides to leave the seed. In other embodiments, the initiation (108) is achieved by the dissolving of the coating due to contact with tissue of the tumor, without further physician initiation.

The alpha-emitter radiotherapy is optionally applied to the patient for at least 24 hours, at least 5 days or even at least 10 days. In some embodiments, the brachytherapy seed is removed from the patient after a designated treatment duration. For example, the seed is optionally removed during surgery for removal of the tumor. Alternatively, the seed is not removed. In some embodiments, the seed comprises a biodegradable material.

The alpha-emitter radiotherapy is optionally initiated only after completion of inducing the ACSIP. During the operation of the alpha-emitter radiotherapy, substances which induce ACSIP are optionally not provided to the patient. In some embodiments, substances which induce ACSIP are not provided to the patient at least 24 hours or even at least a week after completion of the alpha-emitter radiotherapy, for example after removal of the brachytherapy source or sources used. In other embodiments, one or more ACSIP inducing substances are provided while the alpha-emitter radiotherapy is being carried out.

The limited time period (106) between the ACSIP induction (104) and initiating (108) the alpha-emitter radiotherapy, is selected to allow the ACSIP induction to take effect. For example, when the ACSIP is induced by an intracellular viral mimic, the limited time period (106) is selected to serve as a buffering period suitable to allow upregulation of MHC1 expression on the tumor cells' membrane, due to the pathogen mimicry. Alternatively or additionally, the length of the time period (106) is selected as sufficient in order to allow time for the tumor cells to respond to the delivered mimic.

The time period (106) is optionally at least 6 hours, at least 9 hours, at least 12 hours, at least 24 hours or even at least 36 hours, so that the activation of intracellular pathogen recognition begins to take effect before the alpha-emitter radiotherapy is applied. Optionally, the limited time period (106) is shorter than two weeks, shorter than 10 days, shorter than a week, shorter than 120 hours, shorter than 96 hours, shorter than 72 hours or even shorter than 48 hours, so that the effects of the activation of intracellular pathogen recognition are still in effect when the alpha-emitter radiotherapy is applied. In some embodiments, the limited time period (106) is shorter than 30 hours or even shorter than 20 hours, for example in tumors having large numbers of blood vessels or otherwise react more quickly to the ACSIP. When the ACSIP is provided in a plurality of separate sessions, the time period (106) is optionally selected to allow maximal effect of the ACSIP treatment on the patient during the radiotherapy. Optionally, the time span of the ACSIP treatment is less than 10 days, less than a week or even not more than five days, so that the time span from the first ACSIP treatment session is not longer than a desired maximal wait time (e.g., 10 days) between the first ACSIP treatment session and the radiotherapy, and the time between the last ACSIP treatment session and the radiotherapy is not shorter than a minimal desired wait time (e.g., 12 hours).

While the above description relates to applying the alpha-emitter radiotherapy after the ACSIP treatment, in some embodiments of the invention the alpha-emitter radiotherapy is provided substantially concurrently with the ACSIP treatment or even before the ACSIP treatment. The alpha-emitter radiotherapy, is provided to the patient within a given time (e.g., two weeks) before or after the ACSIP treatment, where the given time is selected according to the expected time frame of effect of the treatments.

In some embodiments, after activation of intracellular pathogen recognition, one or more parameters of the tumor are monitored in order to determine a time point most suitable for applying the alpha-emitter radiotherapy. The monitoring optionally includes imaging the tumor, using a suitable modality (e.g., X-ray, ultrasound, PET-CT, MRI, CT) to identify when the tumor begins to change due to the activation of intracellular pathogen recognition. Alternatively, the monitoring includes performing a blood test to identify levels of an attribute. It is noted, however, that in some embodiments the DaRT radiation is applied before the effect of the ACSIP is detectable.

Additional Treatment

Providing (114) the supportive treatment comprises, in some embodiments, providing one or more treatments which counter undesired side effects of the radiotherapy and/or of the ACSIP induction (104). Optionally, the supportive treatment comprises one or more treatments that counter accelerated tissue repair induced by the alpha-emitter radiotherapy, as such accelerated tissue repair will support residual tumor cells and promote tumor recurrence. Alternatively or additionally, the supportive treatment comprises one or more anti-inflammation treatments which downregulate inflammation following tissue damage caused by the radiotherapy and/or the ACSIP. Further alternatively or additionally, the supportive treatment comprises one or more treatments which downregulate checkpoint expression (e.g. PD-L1 expression) caused by the radiotherapy and/or the ACSIP. In some embodiments, the supportive treatment comprises one or more treatments which prevent DNA repair, so as to interfere with attempts of the body of the patient to repair DNA of tumor cells damaged by the radiotherapy. In other embodiments, the supportive treatment comprises one or more treatments which stimulate a viral attack of the ACSIP.

In some embodiment, the supportive treatment includes a treatment which has two or even three of the above listed effects. For example, providing a supportive treatment of administering pomalidomide, has the effect of countering tissue repair, downregulating inflammation and downregulating PD-L1 expression. Berzosertib is another example of a drug which can be used to both prevent DNA repair and to downregulate PD-L1 expression.

In other embodiments, the supportive treatment includes a plurality of different treatments, for example a checkpoint blockade (e.g., Anti-PD-1 and/or CTLA4) together with a TLR3 agonist, which stimulates the ACSIP from outside the tumor cells.

In some embodiments, the supportive treatment comprises a supportive immunomodulation, for example, any of the treatments known in the art for inhibition of immunosuppressor cells, such as myeloid-derived suppressor cells (MDSCs) and/or Tregs inhibitors (e.g., Cyclophosphamide) and/or activation of TLR pathway (TLR agonists). The MDSCs inhibitors include, for example, indoleamine 2,3-dioxygenase 1 (IDO1) inhibitors, such as Epacadostat, TGFb inhibitors, such as Galunisertib, PDE5 inhibitors, such as Sildenafil and/or Cox 2 inhibitors, such as etodolac.

Alternatively or additionally, providing (114) the additional treatment comprises providing an immuno-therapy treatment. The immuno-therapy treatment optionally includes administering a checkpoint blockade, such as one or more of Anti PD-1, anti PD-L1, anti CTLA4, anti TIGIT, anti LAG-3, anti TIM-3, anti CD134 and/or anti CD137. Alternatively or additionally, the immuno-therapy treatment comprises administering one or more pattern recognition receptors and/or agonists, such as TLR7,8 (e.g., MEDI9197, Imiquimode), TLR9 (e.g., MGN1703, SD-101, TLR4, GSK1795091, G100, GLA-SE), TLR3 (e.g., Poly-ICLC) and/or STING (e.g., MIW815).

Alternatively or additionally, the additional treatment comprises administering DNA repair inhibitors of a type found to increase, not to affect or to only minimally impede the immune responses induced by alpha-emitter radiotherapy. In some embodiments, the administered DNA repair inhibitors include ATR inhibitors, for example berzosertib, AZD6738, and/or NU6027. Alternatively or additionally, the DNA repair inhibitors include ATM/ATR inhibitors, such as KU-55933, KU-60019 and/or EPI-46464, DNA-PK inhibitors (e.g., 6-Nitroveratraldehyde, NU7441), Wee1 inhibitors (e.g., adavosertib), Hsp90 inhibitors (e.g., Tanespimycin) and/or PARP inhibitors (e.g., Olaparib, Talazoparib).

Alternatively or additionally, the additional treatment comprises anti-angiogenic factors of a type found to increase, not to affect or to only minimally impede the immune responses induced by alpha-emitter radiotherapy and/or the ACSIP. In some embodiments, the additional treatment comprises iMiDs for example Pomalidomide. Thalidomide. Lenalidomide and/or Apremilast.

Further alternatively or additionally, the additional treatment comprises local or systemic chemotherapy treatment, of a type found not to interfere with the alpha radiation and/or the immune responses to ACSIP and/or the DaRT radiation. Optionally, the chemotherapy treatment comprises one or more of Cyclophosphamide (CP), doxorubicin, mitoxantrone, gemcitabine, oxaliplatin and/or cisplatin.

In some embodiments, the additional treatment comprises checkpoint inhibition by one or more agents or drugs which downregulate the expression of checkpoint molecules, for example pomalidomide (IMiDs), and/or berzosertib (ATR inhibitor).

In some embodiments, the additional treatment comprises alternatively or additionally, anti-inflammatory drugs, such as NSAIDs, e.g., Cox2 inhibitors.

Further alternatively or additionally, the additional treatment comprises administering one or more epigenetic drugs, such as DNMT inhibitors (e.g., Decitabine, Azacytidine, Guadecitabine) and/or HDAC inhibitors (e.g., Entinostat, vorinostat).

In some embodiments, the additional treatment is provided (114) while the alpha-emitter radiation is provided. In other embodiments, the additional treatment is provided (114) after the alpha-emitter radiotherapy is completed, for example after the majority of the radionuclides in the brachytherapy seeds underwent a nuclear reaction, and/or after the brachytherapy seeds are removed from the patient. In still other embodiments, the additional treatment is provided (114) before the alpha-emitter radiotherapy.

In some embodiments, the supportive treatment is provided within less than 72 hours, less than 48 hours or even less than 32 hours from one of the ACSIP sessions and/or the radiotherapy treatment.

The timing of providing the additional treatment is optionally selected according to the specific type of the additional treatment. For example, checkpoint inhibitors, when provided, are administered during or after the alpha-emitter radiotherapy, possibly even 3 days or even a week after beginning the alpha-emitter radiotherapy and/or after completion of the alpha-emitter radiotherapy.

Optionally, the additional treatment is provided (114) responsively to the tumor type.

Treatment Kit

Figure 2:
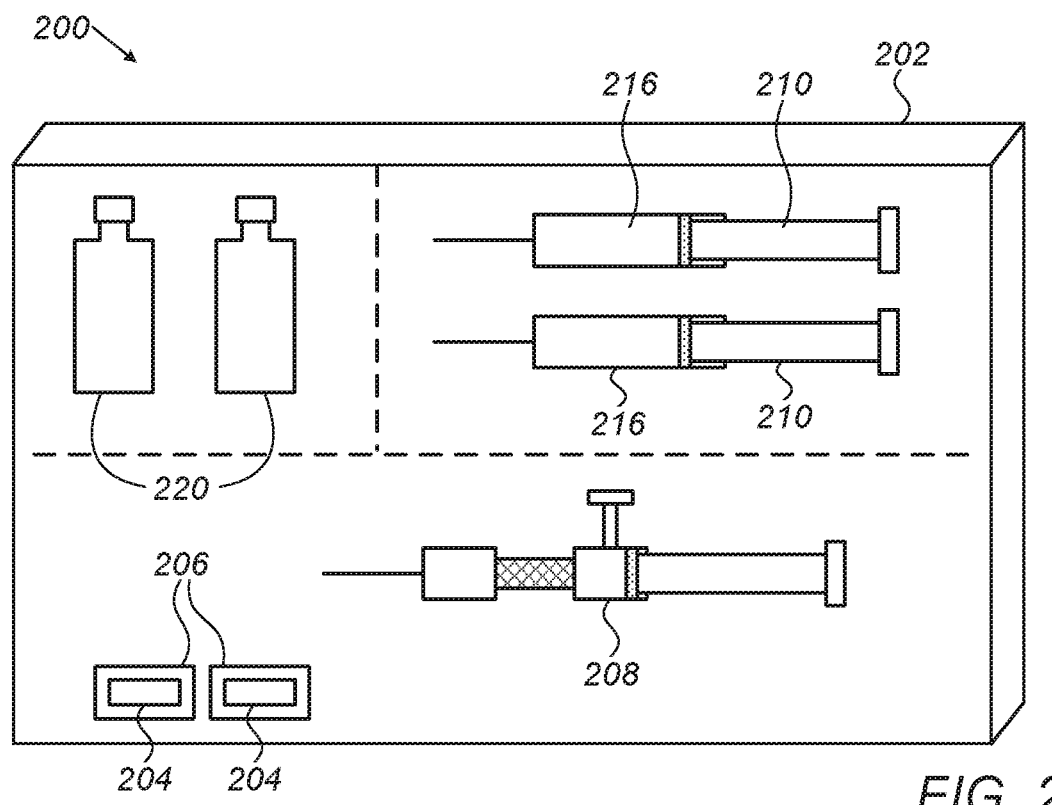
FIG. 2 is a schematic illustration of a kit for combined alpha-emitter radiation and ACSIP, in accordance with an embodiment of the invention.

FIG. 2 is a schematic illustration of a kit 200 for treatment of a patient in accordance with the method of FIG. 1. Kit 200 comprises a sterile package 202 including one or more alpha-emitter radiotherapy seeds 204, for insertion into a tumor, and one or more doses 216 of an agent for ACSIP induction (204).

Optionally, the seeds 204 are provided within a vial or other casing 206 which prevents radiation from exiting the casing. In some embodiments, the casing is filled with a viscous liquid, such as glycerine, which prevents radiation from escaping the casing 206, such as described in PCT application PCT/IB2019/051834, titled "Radiotherapy Seeds and Applicators", the disclosure of which is incorporated herein by reference. In some embodiments, kit 200 further includes a seed applicator 208, which is used to introduce seeds 204 into the patient, as described in PCT application PCT/IB2019/051834. Optionally, applicator 208 is provided preloaded with one or more seeds 204 therein. In accordance with this option, separate seeds 204 in casings 206 are supplied for cases in which more than the number of preloaded seeds is required. Alternatively, seeds 204 in casings 206 are not provided in kit 200 and only seeds within applicator 208 are included in the kit 200.

As shown, the doses 216 of the ACSIP are provided preloaded in one or more needles 210. In other embodiments, the doses 216 are provided in one or more containers or vials and the needles are provided separately within sterile package 202 or are not provided in kit 200, at all.

In some embodiments, kit 200 further includes one or more drugs 220 required for the supportive immuno-modulatory treatments (114).

In some embodiments, kit 200 includes a plurality of separate compartments, separated by suitable insulation, for substances which require storage at different temperatures. For example, a first compartment may include dry ice which keeps the substances in the first compartment at about −20° C., while a second compartment includes ice which keeps the substances in the second compartment at about 4° C.

Experiments

Figure 3:
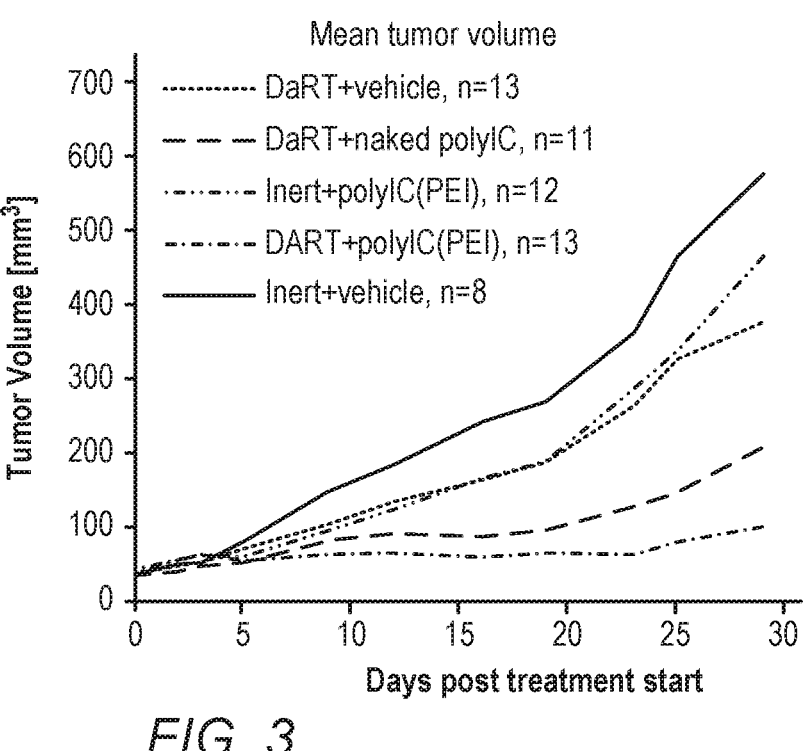
FIG. 3 is a graph showing results of an experiment testing an effect of a combined alpha-emitter radiation and ACSIP treatment on breast cancer tumor development, in accordance with an embodiment of the invention.

FIG. 3 shows the results of an experiment applicant performed to test the method of FIG. 1. In the experiment, high molecular weight (HMW) PolyIC dsRNA viral mimic (20 µg/40 µl) was delivered into the cytoplasm of primary tumor cells in situ, using the delivery agent PEI, in mice bearing 4T1 triple negative breast cancer tumors having a volume of ~40 mm³. PolyIC was complexed with PEI in a ratio of Nucleic acid/Polymer=6. The viral mimic delivery was performed twice, with the second delivery performed 48 hours after the first delivery. The wait time (106) between the second mimic delivery and the initiation of an alpha-emitter radiation treatment by brachytherapy was 24 hours. The alpha-emitter radiation treatment was performed by a 70 kBq (kilo-Becquerel) seed of Radium-224, having a length of 8 mm. A control group of mice received an inert source without Radium-224.

FIG. 3 shows the average tumor volume of the mice 29 days post treatment start on the y-axis, as a function of number of days after the treatment on the X-axis. As can be seen in FIG. 3, the intracellular viral mimic delivery reduces the tumor size by up to about 20%. Alpha-emitter radiation treatment on its own reduces the tumor size by up to about 34%. The combination of alpha-emitter treatment with a naked viral mimic not provided with a delivery reagent, reduces the tumor size by up to about 64%. The combination of alpha-emitter radiotherapy and intracellular viral mimic delivery reduces the tumor size by over 82% which is substantially more than expected for each of the treatments separately.

The following table shows the effect of the method of FIG. 1 on the percent of mice bearing lung metastases using two methods of imaging.

|  | DaRT + PBS | DaRT + PolyIC | Inert + PBS | DaRT + polyIC$^{PEI}$ | Inert + polyIC$^{PEI}$ |
|---|---|---|---|---|---|
| CT | 62 | 55 | 75 | 23 | 57 |
| Fluorescence imaging | 77 | 55 | 75 | 23 | 57 |

The table summarizes the results in the mice participating in the experiment described in FIG. 3, as measured by CT or M-Cherry fluorescent imaging, 29 days after the first viral mimic delivery. The numbers in the table indicate the percentage of mice that were positive for lung metastases. A significantly greater number of mice was negative for lung metastases in the group receiving the combined alpha-emitter radiation and intracellular viral mimic delivery treatment (77% metastases-free), relative to those receiving separate treatments, or PolyIC without PEI in combination with DaRT.

Another experiment was performed to test the effect of the method of FIG. 1 on long term immune response. Mice bearing 4T1 tumors (30 mm$^3$) were treated with the combined alpha-emitter radiotherapy and intracellular viral mimic delivery treatment (same treatment protocol as described in FIG. 3, seed data: 7 mm, 80 kBq; 20 µg/40 µl polyIC$^{PEI}$). Residual tumors were resected 24 days following tumor cell inoculation and animals were observed for long term survival (metastases related death), and investigated for long term immune memory. Twenty five percent (4 out of 16) of the mice survived for 9 months since inoculation, indicating metastases clearance. Whereas, 100% of mice inoculated with the same number of tumor cells that were treated with an inert seed and intratumoral PBS, and their tumor was resected prior to this timepoint (day 17) already developed lung metastases. The spleens of surviving (cured) mice were harvested and splenocytes were mixed with tumor cells in a ratio of 100:1 (splenocytes: tumor cells). The mixed suspension was inoculated to naïve mice. Splenocytes of naïve mice served as control. Splenocytes of mice treated with DaRT and polyIC$^{PEI}$ significantly retarded tumor development compared to splenocytes of naïve mice. Tumor retardation by up to 48%, lasted up to 19 days since co-inoculation of splenocytes with tumor cells, demonstrating that the treatment induced a long-term immune memory that is efficient even following 9 months.

In a further experiment, applicant tested the method of FIG. 1 combined with an additional immunomodulatory treatment, which inhibit T-regulatory cells, by using low dose Cyclophosphamide (100 mg/kg, one day prior the treatment start, i.e., first polyIC$^{PEI}$ injection). The experiment was performed on mice bearing 4T1 tumors (25 mm$^3$) with DaRT seeds of 6.5 mm and 65 kBq, and ACSIP of 30 µg/60 µl polyIC$^{PEI}$. Adding T-regulatory cell inhibition further retard tumor development compared to the DaRT with polyIC$^{PEI}$ treatment by up to 43%. Moreover, following tumor resection (24 days after tumor inoculation), the additional treatment by CP did not reduce long-term survival rates, which were 71% in both groups at the end of the experiment (180 days post-DaRT). However, it extended the survival period by 30%, so that for example during the period between 85 and 145 days post-DaRT, 100% of the mice were alive in the group treated with DaRT, polyIC$^{PEI}$ and CP, compared with 71% in the group treated with DaRT and polyIC$^{PEI}$. In addition, both the treatment by DaRT+polyIC$^{PEI}$ and the treatment by DaRT+polyIC$^{PEI}$ combined with an additional dose of Cyclophosphamide induced long term immune memory and delayed tumor re-challenge development in treated (cured) mice compared to naïve mice. Furthermore, the applicant performed an additional experiment to test the method of FIG. 1 combined with Cyclophosphamide under neoadjuvant settings which enables the comparison of long-term survival rates following the combined treatment to those of its separate components: DaRT alone and immunomodulation by CP and polyIC$^{PEI}$ alone. Mice bearing 4T1 tumors (23 mm$^3$) were treated with CP followed by two doses of 30 µg/60 µl polyIC$^{PEI}$ as described above, and an insertion of a 6.5 mm, 85 Kbq DaRT seed. Residual tumors were excised 14 days after DaRT (24 days since tumor inoculation). Inert seeds and vehicle injections served as controls. The treatment of FIG. 1, when used as a neoadjuvant treatment, combined with Cyclophosphamide prevented metastases formation and cured mice in 75% of mice whereas only 33% were cured using DaRT alone, 25% were cured using polyIC$^{PEI}$+ CP+inert seed, and 12% using an inert seed and vehicle injections. Cure of mice was defined as survival more than 155 days since inoculation.

Additionally, an experiment was performed by applicant to test the method of FIG. 1 by the induction of ACSIP via stimulation of an endogenous pathogen using low-dose Decitabine, and to compare the effect of this treatment on tumor development to the effect of the viral mimic delivery polyIC$^{PEI}$. SQ2 (squamous cell carcinoma)—bearing mice were treated with 85 Kbq DaRT seeds and 25 µg/50 µl polyIC$^{PEI}$72 and 24 hours prior to the DaRT or Decitabine in the dose of 1 mg/kg i.p. for 4 days prior to DaRT, daily. Alpha-emitter radiation treatment combined with Decitabine retarded tumor development similarly to alpha-emitter radiation treatment combined with polyIC$^{PEI}$ delivery, both treatments retarded tumor development in about 66% compared to DaRT alone. In addition, the treatment preserved the ability to induce long term immune memory as demonstrated in improved retardation of re-challenge tumor development of about 82% in treated and tumor-resected mice, compared to naïve mice inoculated with the same number of tumor cells.

Two additional experiments were performed by applicant to test the method of FIG. 1 by the induction of ACSIP via stimulation of endogenous pathogen using low-dose Decitabine in 4T1 breast cancer mice model (large tumors). Mice were treated with a 75 kBq DaRT seed and 30 µg/60 µl polyIC$^{PEI}$, 72 hours prior to DaRT and 50 µg/100 µl polyIC$^{PE}$ 24 hours prior DaRT or Decitabine in a dose of 1 mg/kg i.p. at 4 days prior to DaRT, daily. Alpha-emitter radiation treatment combined with Decitabine retards tumor development similarly to polyIC$^{PEI}$ also in 4T1 breast mice model by 64%, compared to DaRT alone. Moreover, it showed that when DaRT was combined with both Decitabine and polyIC$^{PEI}$, the effect was doubled compared to the same treatment with a non-radioactive seed, and was 4-fold compared to DaRT alone. Furthermore, it shows that in this cancer model, activating TLR3 pathway by the TLR3 agonist "naked" polyIC (without PEI), in addition to Decitabine and DaRT, improves the outcome in 41% relative to activating the same RIG-1 pathway by combining Decitabine and polyIC$^{PEI}$ and DaRT.

Finally, an experiment testing the method of FIG. 1, in the murine pancreatic tumor model Panc02 was performed by the applicant. In addition, the treatment was tested in combination with iMiD drug Pomalidomide (POM) in this model.

Eleven days following inoculation, tumors with a volume of 22 mm$^3$, received a first intratumoral injection of polyIC$^{PEI}$ at a dose of 30 µg/60 µl, followed by a second dose 48 hours later. A DaRT seed (6.5 mm 75 kBq) was inserted to the tumor 24 hours after the last polyIC$^{PEI}$ injection. Four days later 25 mg/kg POM were injected i.p. in a volume of 300 µl every other day for 5 days, beginning on the 4th day after DaRT.

Alpha-emitter radiation treatment combined with polyIC$^{PEI}$ eliminated the pancreatic tumors in 30% of the mice. Adding the iMiD drug Pomalidomide increased rejection rate to 50%, whereas no tumor rejection was observed in groups treated by DaRT alone or DaRT+Pomalidomide or inert seed+Pomalidomide+polyIC$^{PEI}$.

CONCLUSION

It will be appreciated that the above described methods and apparatus are to be interpreted as including apparatus for carrying out the methods and methods of using the apparatus. It should be understood that features and/or steps described with respect to one embodiment may sometimes be used with other embodiments and that not all embodiments of the invention have all of the features and/or steps shown in a particular figure or described with respect to one of the specific embodiments. Tasks are not necessarily performed in the exact order described.

It is noted that some of the above described embodiments may include structure, acts or details of structures and acts that may not be essential to the invention and which are described as examples. Structure and acts described herein are replaceable by equivalents which perform the same function, even if the structure or acts are different, as known in the art. The embodiments described above are cited by way of example, and the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art. Therefore, the scope of the invention is limited only by the elements and limitations as used in the claims, wherein the terms "comprise," "include," "have" and their conjugates, shall mean, when used in the claims, "including but not necessarily limited to."

The invention claimed is:

1. A method of treating a patient with a tumor, comprising:
   administering, to the patient, a substance including a pathogen mimic with a delivery agent suitable for cytoplasmic delivery of the pathogen mimic; and
   treating the tumor with intra-tumoral alpha-emitter radiotherapy within two weeks of administering the substance.

2. The method of claim 1, wherein administering the pathogen mimic together with a delivery agent comprises administering a single dose of the pathogen mimic in a single session.

3. The method of claim 1, wherein administering the pathogen mimic together with a delivery agent comprises administering at least three doses of the pathogen mimic in respective separate sessions.

4. The method of claim 1, wherein administering the substance comprises administering the substance with a delivery agent suitable for targeted delivery.

5. The method of claim 1, wherein the delivery agent comprises a lipid based delivery agent.

6. The method of claim 1, wherein the delivery agent comprises a polymer based delivery agent.

7. The method of claim 1, wherein the delivery agent comprises a cationic polymer complex or a cationic lipid.

8. The method of claim 1, wherein the delivery agent comprises a liposome or a lipoplex.

9. The method of claim 1, wherein the delivery agent comprises polymeric micelles.

10. The method of claim 1, wherein the delivery agent comprises a solid nanoparticle.

11. The method of claim 1, wherein the delivery agent comprises a metal-based nanoparticle system.

12. The method of claim 1, wherein the delivery agent comprises polyethylenimine (PEI).

13. The method of claim 1, wherein administering the pathogen mimic comprises administering a bacteria mimic.

14. The method of claim 1, wherein administering the pathogen mimic comprises administering a viral mimic.

15. The method of claim 14, wherein administering the viral mimic comprises administering double stranded RNA (dsRNA).

16. The method of claim 15, wherein administering the dsRNA comprises administering polyIC.

17. The method of claim 16, wherein the delivery agent comprises polyethylenimine (PEI).

18. The method of claim 15, wherein administering the dsRNA comprises administering 5' ppp-dsRNA.

19. The method of claim 15, wherein administering the dsRNA comprises administering 3p-hpRNA.

20. The method of claim 15, wherein administering the dsRNA comprises administering Poly(dA:dT).

21. The method of claim 15, wherein administering the dsRNA comprises administering poly-ICLC.

22. The method of claim 15, wherein administering the dsRNA comprises administering poly(A:U).

23. The method of claim 15, wherein administering the dsRNA comprises administering CpG rich RNA.

24. The method of claim 1, wherein administering the pathogen mimic comprises administering a pathogen mimic that is recognized by intracellular receptors as non-self.

25. The method of claim 1, further comprising administering an agent which induces production of molecules, which stimulate cytoplasmatic sensors for an intracellular pathogen, within cells of the tumor.

26. The method of claim 25, wherein administering the agent comprises administering a DNA methyltransferase (DNMT) inhibitor.

27. The method of claim 26, wherein administering the DNA methyltransferase (DNMT) inhibitor comprises administering Decitabine.

28. The method of claim 26, wherein administering the DNA methyltransferase (DNMT) inhibitor comprises administering Azacytidine.

29. The method of claim 26, wherein administering the DNA methyltransferase (DNMT) inhibitor comprises administering Guadecitabine.

30. The method of claim 25, wherein administering the agent comprises administering a histone deacetylase (HDAC) inhibitor.

31. The method of claim 30, wherein administering the histone deacetylase (HDAC) inhibitor comprises administering Entinostat.

32. The method of claim 30, wherein administering the histone deacetylase (HDAC) inhibitor comprises administering vorinostat.

33. The method of claim 25, further comprising additionally administering to the patient a supportive treatment of cyclophosphamide.

34. The method of claim 1, wherein treating the tumor with alpha-emitter radiotherapy comprises inserting a source carrying alpha-emitting radionuclides into the tumor.

35. The method of claim 34, wherein the source releases alpha-emitting radionuclides at a rate of less than 25% of the alpha-emitting radionuclides on the source when inserted to the tumor, per day.

36. The method of claim 34, wherein the source comprises a Radium source.

37. The method of claim 1, wherein treating the tumor with alpha-emitter radiotherapy is performed only after completing the administering of the substance.

38. The method of claim 1, wherein administering the substance comprises administering with nanoghosts, which direct the substance to the tumor.

39. The method of claim 1, wherein administering the substance comprises administering one or more substances in at least two separate sessions separated from each other by at least 12 hours.

40. The method of claim 39, wherein administering the one or more substances comprises administering in at least three separate sessions separated from each other by at least 20 hours.

41. The method of claim 1, and further comprising identifying a primary tumor in the patient and wherein administering the substance comprises administering the substance to the identified primary tumor.

42. The method of claim 1, wherein treating the tumor with alpha-emitter radiotherapy comprises treating with alpha-emitter radiotherapy less than 80 hours after administering a last dose of the substance.

43. The method of claim 1, wherein treating the tumor with alpha-emitter radiotherapy comprises treating with alpha-emitter radiotherapy less than 60 hours after administering a last dose of the substance.

44. The method of claim 1, wherein treating the tumor with alpha-emitter radiotherapy comprises treating with alpha-emitter radiotherapy at least 24 hours after administering a last dose of the substance.

45. The method of claim 1 further comprising additionally administering to the patient a supportive treatment which counters accelerated tissue repair induced by the alpha-emitter radiotherapy.

46. The method of claim 1 further comprising additionally administering to the patient a supportive treatment which downregulates inflammation.

47. The method of claim 1 further comprising additionally administering to the patient a supportive treatment which downregulates checkpoint expression.

48. The method of claim 1 further comprising additionally administering to the patient a supportive treatment of cyclophosphamide.

49. The method of claim 1 further comprising additionally administering to the patient a supportive treatment of pomalidomide.

50. The method of claim 1 further comprising additionally administering to the patient a supportive treatment of berzosertib.

51. The method of claim 1 further comprising additionally administering to the patient a supportive treatment of a checkpoint blockade.

52. The method of claim 51, further comprising additionally administering to the patient a supportive treatment of anti PD-1.

53. The method of claim 51, further comprising additionally administering to the patient a supportive treatment of anti-PD-L1.

54. The method of claim 51, further comprising additionally administering to the patient a supportive treatment of anti-CTLA4.

55. The method of claim 1, further comprising additionally administering to the patient a supportive treatment of one or more TLR agonists.

56. The method of claim 1, further comprising additionally administering to the patient a supportive treatment of one or more MDSCs inhibitors.

57. The method of claim 1, further comprising additionally administering to the patient a supportive treatment of one or more Tregs inhibitors.

58. The method of claim 1, further comprising additionally administering to the patient a supportive treatment of one or more DNA repair inhibitors.

59. The method of claim 1, further comprising additionally administering to the patient a supportive treatment of one or more Antiangiogenic factors.

60. The method of claim 1, further comprising performing surgery to remove the tumor, at least a week after beginning treating the tumor with alpha-emitter radiotherapy.

61. The method of claim 1, wherein treating the tumor with intra-tumoral alpha-emitter radiotherapy comprises treating the tumor with intra-tumoral alpha-emitter radiotherapy less than a week after administering the substance which activates cytoplasmatic sensors for intracellular pathogen in the tumor.

62. The method of claim 1, wherein administering the substance comprises administering an oncolytic virus.

63. The method of claim 1, wherein the pathogen mimic comprises a STING ligand.

* * * * *